(12) United States Patent
Tarur et al.

(10) Patent No.: US 7,378,439 B2
(45) Date of Patent: May 27, 2008

(54) PROCESS FOR THE PREPARATION OF 4-(2-DIPROPYLAMINOETHYL)-1,3-DIHYDRO-2H-INDOL-2-ONE HYDROCHLORIDE

(75) Inventors: Venkatasubramanian Radhakrishna Tarur, Mumbai (IN); Dhananjay Govind Sathe, Thane (IN); Harish Kashinath Mondkar, Mumbai (IN); Rajesh Ganpat Bhopalkar, Naupada (IN); Samadhan Daulat Patil, Dombivli (IN)

(73) Assignee: USV, Ltd., Mumbai (IN)

( * ) Notice: Subject to any disclaimer, the term of this patent is extended or adjusted under 35 U.S.C. 154(b) by 200 days.

(21) Appl. No.: 10/888,901

(22) Filed: Jul. 9, 2004

(65) Prior Publication Data

US 2005/0159605 A1    Jul. 21, 2005

(30) Foreign Application Priority Data

Jan. 20, 2004    (IN) .......................... 60/MUM/2004

(51) Int. Cl.
*A61K 31/4015*    (2006.01)
*C07D 209/34*    (2006.01)

(52) U.S. Cl. ...................................... 514/418; 548/486

(58) Field of Classification Search ................ 548/486; 514/418
See application file for complete search history.

(56) References Cited

OTHER PUBLICATIONS

Hayler, et al. Organic Process Research & Development, 1998, 2, pp. 3-9.*

* cited by examiner

*Primary Examiner*—Joseph McKane
*Assistant Examiner*—Shawquia Young
(74) *Attorney, Agent, or Firm*—Pharmaceutical Patent Attorneys, LLC

(57) ABSTRACT

The present invention discloses a novel process and novel intermediates for the Preparation of 4-[2-(di-n-propyl amino) ethyl]-1,3-dihydro-2H-indol-2-one, commonly known as Ropinirole (I) and pharmaceutical composition comprising the same. Further the present invention also discloses a method of treatment for cardiovascular disorders and Parkinson's disease.

24 Claims, No Drawings

PROCESS FOR THE PREPARATION OF 4-(2-DIPROPYLAMINOETHYL)-1,3-DIHYDRO-2H-INDOL-2-ONE HYDROCHLORIDE

RELATED APPLICATION

This application claims priority from India National patent application serial No. 60/MUM/2003, filed 20 Jan 04.

TECHNICAL FIELD OF INVENTION

The present invention relates to a novel process and novel intermediates for the preparation of 4-[2-(di-n-propyl amino)ethyl]-1,3-dihydro-2H-indol-2-one, commonly known as Ropinirole.

BACKGROUND AND PRIOR ART

Ropinirole is described in U.S. Pat. No. 4,452,808 as being useful in cardiovascular therapy and in U.S. Pat. No. 4,824,860 as an agent useful in treating Parkinson's disease. The processes for the preparation of Ropinirole HC 1 and its derivatives have previously been described. U.S. Pat. No. 4,452,808 describes the preparation of 4-aminoalkyl-2(3H)-indolones staring from either 4-aminoalkyl-7-hydroxy-2(3H)-indolones or 2-methyl-3-nitro-benzene acetic acid by two different processes. Particularly those processes involving reductive cyclization of nitrostyrene intermediates in presence of acetyl chloride and Iron (III) chloride described in EP 0300614 and WO 91/16306 are of particular relevance. Present invention discloses a novel route and novel intermediates for the preparation of Ropinirole. Present invention comprises of 6 steps leading to desired moiety.

U.S. patents namely U.S. Pat. No. 4,452,808, U.S. Pat. No. 5,336,781, U.S. Pat. No. 4,997,954, U.S. Pat. No. 4,314,944 molecule called Ropinirole. For the present purpose U.S. Pat. No. 4,452,808 and U.S. Pat. No. 4,314,944 are more relevant. Few patents deal with Ropinirole mainly from method of treatment point of view and therefore are not directly related to the present invention.

WO 91/16306 and EP 0300614 are relevant from the point of view of reductive cyclization and are dealt at appropriate place hereafter.

The processes for the preparation of Ropinirole HCl and its derivatives have previously been described. U.S. Pat. No. 4,452,808 describes the preparation of 4-aminoalkyl-2(3H)-indolones starting from either 4-aminoalkyl-7-hydroxy-2(3H)-indolones or 2-methyl-3-nitro-benzene acetic acid by two different processes. The 7-hydroxy intermediate (i) is first converted to its tetrazolo derivative (ii) which is then hydrogenated to get Ropinirole as shown in Scheme 1. Preparation of 7-hydroxy intermediate (i) is described in U.S. Pat. No. 4,314,944 by following a series of steps starting from p-methoxy phenethylamine. Second process described in U.S. Pat. No. 4,452,808 allows preparation of Ropinirole by following a series of steps starting from 2-methyl-3-nitro benzeneacetic acid.

Scheme I

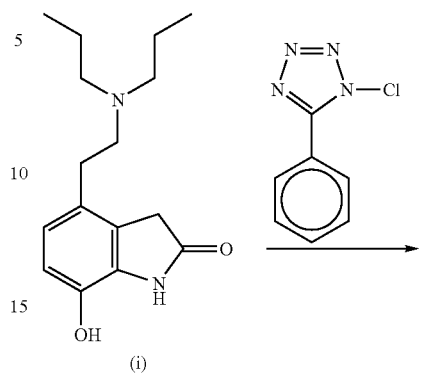

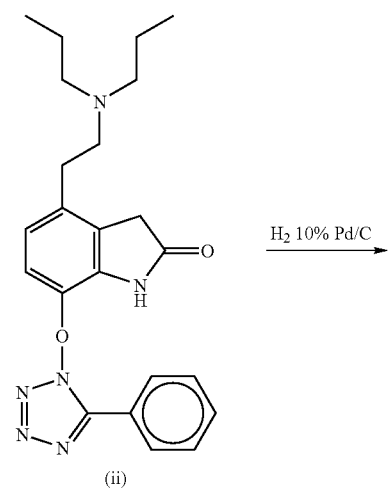

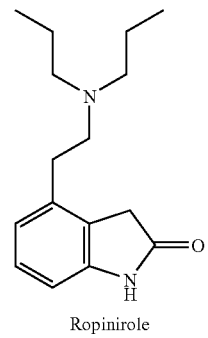

Ropinirole

Particularly those processes involving reductive cyclization of nitro styrene intermediates in presence of acetyl chloride and Iron (III) chloride described in EP 0300614 and WO 91/16306, are of relevance, as far as this invention is concerned.

Scheme 2 depicts the route disclosed in EP0300614. EP0300614 describes the preparation of Ropinirole by condensation of 4-[2-(bromoethyl)-1,3-dihydro-2H-indol-2-one (iii) with di-n-propyl amine (iv). The intermediate (iii) is prepared by following a series of steps starting from 2-(2-bromoethyl)benzaldehyde. Major drawback is a possible formation of an elimination product due to loss of HBr as shown in Scheme 2. Such reaction can impact the purity of desired product and can influence the yield aspects.

Scheme 2

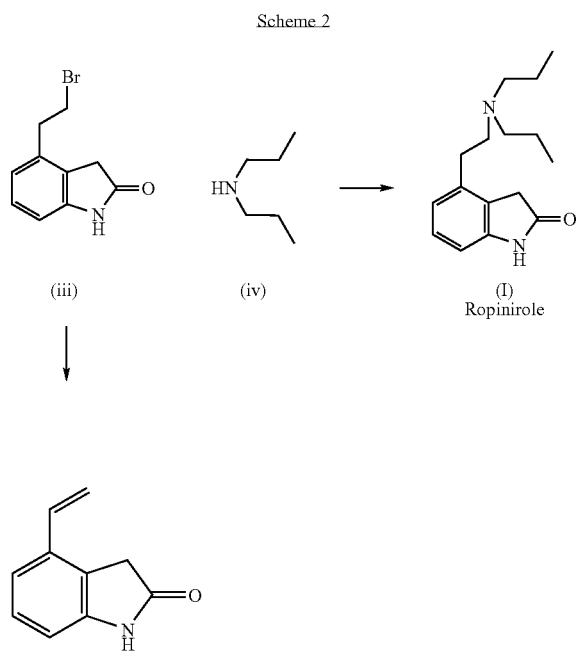

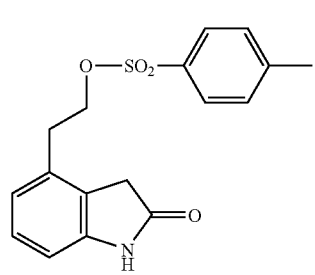

Elimination Product

The process as described in WO 91/16306 is an improved process for the preparation of Ropinirole comprising of number of steps, total of eight starting from Isochroman, to get the final product Ropinirole. It discloses the route wherein condensation of di-n-propylamine with a novel intermediate of formula (v) is carried out. Intermediate (v) is prepared by series of steps starting from Isochroman. The process involves well over 7 steps and therefore is a longer one.

(v)

moiety from oxindole leads to formation of aminoethyloxindole. N-alkylation reaction comprising of reductive alkylation or direct alkylation of aminoethyloxindole gives Ropinirole.

Further a pharmaceutical composition comprising a therapeutically effective amount of 4-[2-(di-n-propyl amino) ethyl]-1,3-dihydro-2H-indol-2-one is also disclosed.

A method of treating Parkinson's disease or cardiovascular disorders, the method comprising administering to a patient an effective amount of a product-by-process composition of matter comprising 4-(2-Dipropylaminoethyl)-1,3-dihydro-2H-indol-2-one or its salt wherein the said 4-(2-Dipropylaminoethyl)-1,3-dihydro-2H-indol-2-one or its salt manufactured by the said process is also envisaged as part of this invention.

DETAILED DESCRIPTION OF THE INVENTION

The Gabriel synthesis is well known in the art and consists of treatment of alkyl halide with Potassium pthalimide to form an intermediate N-alkyl phthalimide followed by deprotection to give primary alkyl amine.

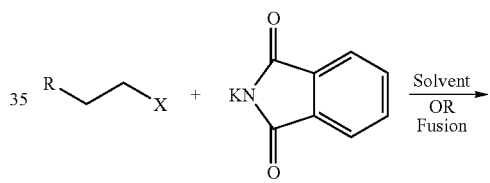

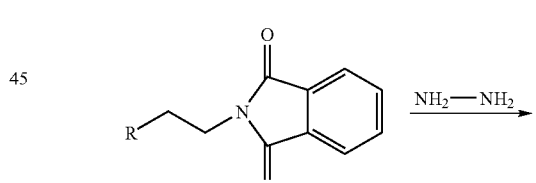

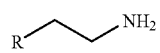

SUMMARY OF THE INVENTION

The process comprises condensation reaction of 2-(2'-bromoethyl)benzaldehyde and an alkali metal salt of an imide like Potassium Phthalimide to give a Phthalimido derivative. Use of suitable solvent is made of for smooth reaction. Phthalimido derivative is converted to nitrostyrene derivative by modified Henry reaction. This is made to undergo Royer reaction to give chloro-oxindole derivative. Dechlorination of this chloro-oxindole derivative gives Phthalimido oxindole product. Removal of Phthalimide In the present invention the Gabriel synthesis is employed to introduce the amino group at the 2 position of ethyl side chain. The process disclosed in the present invention describes preparation of Ropinirole from commercially available 2-(2'-Bromoethyl) benzaldehyde in six synthetic steps and is economical.

The novel process of the present invention can be depicted as shown in the scheme 3.

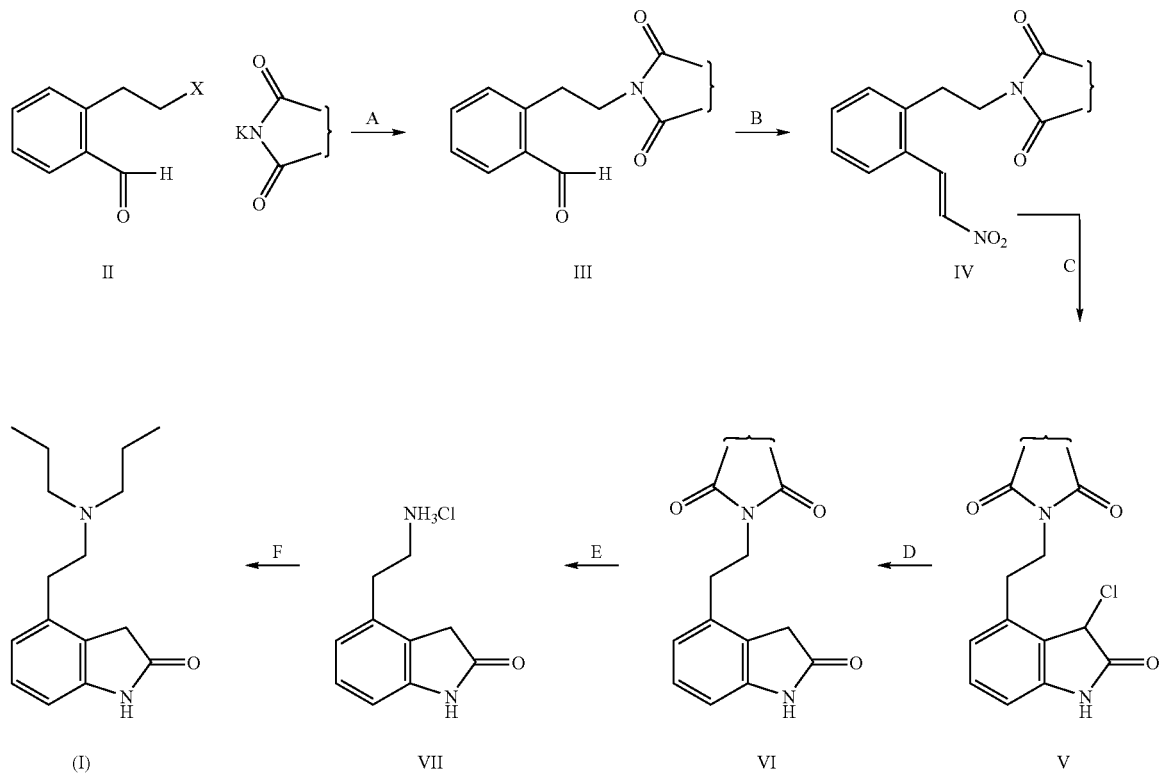

Scheme-3

Step A of scheme 3 is a condensation reaction between 2-(2'-haloethyl) benzaldehyde and an alkalimetal salt of an imide such as potassium phthalimide or potassium maleimide, carried out with solvent, preferably in any of the solvent from the class of dipolar aprotic or a lower aliphatic alcohol or an aromatic hydrocarbon or lower aliphatic ketones at temperatures ranging from 0 to 150° C. for 1 to 12 hrs followed by isolation of the product directly as a solid by dilution with water followed by filtration or by evaporation of the solvent The reaction is preferably carried out between 2-(2'-bromo ethyl) benzaldehyde (II, X=Br) and potassium phthalimide in a dipolar aprotic solvent, more preferably in DMF, at temperature range of 30-60° C. for 5 to 12 hrs followed by isolation of III by quenching the reaction mass in water followed by filtration.

Dipolar aprotic solvents are to be construed to mean those solvents, which are so recognized by those skilled in the art. Nonlimiting examples are DMSO, DMF, Acetone.

A lower aliphatic alcohol is to be construed to mean alcohol having a molecular formula comprising of number of carbon atoms either four or less than four including branched chain alcohols. Nonlimiting examples are methanol, ethanol, propanol, isopropyl alcohol, butyl alcohol, tert-butyl alcohol, iso-butyl alcohol. An aromatic hydrocarbon is to be construed to mean one with unsaturated character and a closed ring structure. Nonlimiting examples are benzene, toluene, xylene. A lower aliphatic ketone is to be construed to mean a ketone where total number of carbons is 3 to 6. Nonlimiting examples are acetone, ethyl methyl ketone.

Step B is a modified Henry reaction. These modifications are to suit the specific purpose of end product to be achieved at the end of stage. It comprises of charging sequentially molar equivalents of nitromethane, acetic acid, n-butylamine and 1 to 2 mole excess of trimethyl orthoformate to a suspension of III in lower aliphatic alcohols preferably methanol and stirring at a temperature range of 30 to 80° C. for 15 to 30 hours until the reaction is complete. Completion of reaction can be judged by conventional TLC techniques. The product IV is isolated by filtration.

Step C is a reductive cyclization of IV comprising of charging of a lower aliphatic acid chloride such as Valeryl Chloride, acetyl chloride, pivalyl chloride, preferably valeryl chloride to a stirred solution of Nitrostyrene (IV) and 3 to 5 molar equivalent of Ferric Chloride in Dichloromethane at 0 to 5° C. and stirring the reaction in the range of −10 to 30° C. preferably 0 to 10° C. for about 18 to 24 hrs until the reaction is complete, The reaction is quenched by adding the mixture to water and the product V is isolated by filtration.

Step D, is the dechlorination step, comprising charging sequentially a hydrogenation catalyst such as Raney Nickel supported palladium or platinum preferably supported palladium on carbon, an aqueous solution of 5 to 10 molar excess of hydrogen donors like Sodium hypophosphite, hydrazine hydrate, formates, preferably sodium hypophosphite to a solution of V in ethyl acetate and string at reflux for about 2 to 4 hrs till the reaction is complete. The suspension is filtered, the cake is extracted in hot acetic acid, the catalyst is filtered and acetic acid filtrate is quenched in water. The product VI is isolated by filtration.

Step D can also be performed in another way. This alternative route comprises of hydrogenating a solution of V in DMF in presence of a reduction catalyst such as Raney Ni or supported Platinum or palladium or under Hydrogen pressure ranging from atmospheric to 10 Kg preferably 5 Kg at temperatures room temperature to 100° C., preferably 60° C. and isolating the product VI by filtration of catalyst and evaporation of DMF.

Step E, is a deprotection step comprising stirring alcoholic solution of VI, preferably methanolic solution with 1 to 4 molar equivalents of hydrazine hydrate at 30 to 60° C. till precipitation is complete. The resulting suspension is treated with 1 to 10 molar excess of acid lke hydrochloric acid, aqueous, hydrobromic acid, acetic acid preferably acetic acid and the mass is digested at 30-80° C. for 0.5 to 2 hrs. The reaction mass is filtered and filtrate solvent is evaporated and the residue is slurried in solvents like ethanol, isopropyl alcohol, ethyl acetate. The product VII is isolated by filtration as an acid addition salt.

Step E, a deprotection, can also comprise of refluxing an alcoholic solution, preferably Methanolic solution in presence of 2 to 2.5 molar equivalents of alkali metal hydroxides such as sodium hydroxide, potassium hydroxide, Calcium hydroxide, preferably sodium hydroxide till the reaction is complete. Solvent is evaporated and the product is extracted in a suitable solvent like ethyl acetate, tetrahydrofuran, 1,4-dioxane, dichloromethane preferably ethyl acetate.

Step F, an N-alkylation reaction, comprises reductive alkylation or direct alkylation, preferably reductive alkylation. The reductive alkylation comprises reduction of schiff's base generated by reaction between 4-(2-aminoethyl)-2(3H)-indolone (VII) or its acid addition salt with propionaldehyde in an alcohol or acetic acid or ethyl acetate preferably methanol using either a hydride reducing agent or catalytic reduction, preferably catalytic hydrogenation. The catalytic ydrogenation is carried out using catalysts such as Raney Ni, Noble metal catalysts with or without support preferably Noble metal catalysts with support, most preferably Palladium supported on "Activated charcoal", under Hydrogen pressure ranging from atmosphere to 100 psi, at temperature ranging from room temperature to 100° C., for 5 to 10 hrs till the reaction is complete. The catalyst is then filtered, solvent is evaporated and residue triturated with lower aliphatic alcohol preferably Isopropyl alcohol to get (I).

Direct alkylation comprises charging sequentially alkyl halide (in this case propyl halide) or alkyl sulfonate ester preferably propyl bromide, a base such as alkali metal hydroxide or carbonate or bicarbonate or trialkyl amine or pyridine preferably alkali metal carbonate most preferably sodium carbonate to a solution of VII or its acid addition salt in a suitable solvent such as water, dipolar aprotic solvent, lower aliphatic alcohol, ketones, aromatic hydrocarbons, esters or ethers preferably dipolar aprotic solvent, most preferably DMF and stirring at a temperature in range of 0 to 100° C. for about 2 to 24 hrs till the reaction is complete. The reaction is quenched by adding the mixture to water, extraction with an organic solvent such as ethyl acetate and optionally converting it to its acid addition salt by treating the extract with inorganic acid or an organic acid preferably hydrochloric acid.

EXAMPLES

Example—1

Preparation of 2-(2'-phthalmidoethyl) Benzaldehyde (III)

To a stirred suspension of potassium phthalimide (1.3 Kg, 7 mol) in DMSO (2.5 L), at 110° C., was added 2-(2'-bromoethyl) benzaldehyde (1 Kg, 4.69 mol) added through a dropping funnel over the period of 0.5 hr. The reaction mixture was then stirred at 110° C. for 2.5 hr and cooled to room temperature before being added over the period of 0.5 hr in water (7.5 L). The cream colored solid was filtered at suction, washed with water till neutral and dried overnight at 70° C. This gave the title compound, 1.07 Kg (81.6%) in the form of off white solid.

MS-m/z M+H=280

NMR (200 MHz) DMSO d 3.43 (t, 2H, CH2-Ar); d 4.0 (t, 2H, CH2N); d 7.25-7.89 (m, 8H, Ar—H); d 10.27 (s, 1H, —CHO).

Example—2

Preparation of 2-(2'-phthalimido Ethyl) β-nitrostyrene (IV)

To a stirred suspension of 2-(2'-phthalimidoethyl) benzaldehyde (900 gm, 3.22 mol), in methanol (9.0 Lt) were added nitromethane (521 ml, 9.65 mol), acetic acid (349 ml, 6.1 mol), n-butyl amine (486 ml, 4.72 mol) and trimethyl orthoformate (499 ml, 3 mol) at room temperature. The reaction mixture was then stirred at 30-40° C. for 30 hrs. The greenish coloured solid was filtered at suction, washed with chilled methanol (700 ml) and dried at 50° C. for 8 hrs. This gave the title compound, 649 gm, (62.5%) in the form of cream coloured solid MS-m/z M+H=323.

NMR (200 MHz) DMSO; d 3.17 (t, 2H, CH2-Ar); d 3.91 (t, 2H, CH2N); d 7.26-7.64 (m, 8H Ar—H); d 8.39 (d, 2H, CH═CH).

Example—3

Preparation of 4-(2'-phthalimidoethyl)-3-chloro-1,3-dihydro-2H-indol-2one (V)

To a stirred solution of 2-(2'-phthalimido ethyl)-β-nitrostyrene (25 gm 0.0776 mol) in dichloromethane (500.0 ml) was added Ferric chloride (62.5 gm, 0.385 mol) at room temperature. The reaction mass was cooled to 3° C. and to it was charged valeryl chloride (25 ml, 0.206 mol). The reaction mixture was then stirred at 2-5° C. for 24 hrs before being added to ice cold water (750 ml). The quenched reaction mixture was stirred at 5° C. for 1 hr before being filtered. The yellow solid was isolated at suction, washed with chilled water (2 Lt) and dried at 50 DC for 14 hrs. This gave the title compound, 14 gm, (53%) in the form of cream coloured solid.

MS-m/z M+H=341

NMR (200 MHz) DMSO; d 3.07 (t, 2H, CH2-Ar); d 3.99 (t, 2H, CHz-N); d 5.7 (s, IH COCH)

d 6.83 (d, 1H, Ar—H); d 6.95 (d, 1H, Ar—H); d 7.29 (t, 1H, Ar—H); d 7.9 (s, 4H, ArH); 10.85 (s, 1H, NH).

Example—4

Preparation of 4-(2'-phthalimido Ethyl)-1,3-dihydro-2H-indol-2-one (VI)

4-(2'-phthalmidoethyl)-3-chloro-1,3-dihydro-2H-indol-2-one (47 gm, 0.138 mol) and 10% Pd/C (containing 50% w/w water, 8 gm) were stirred in ethyl acetate (940 Ml) and heated to reflux. To this mixture was added aqueous solution of sodium hypophosphite (47 gm, 0.443 mol) in water (168 ml) over the period of 20 minutes. The reaction mixture was heated for further 90 minutes before being cooled to room temperature. The reaction mixture was filtered through Whatmann filter paper and he cake was added to acetic acid (425 ml). The acetic acid suspension was heated for 1 hr at 110° C. before being filtered hot through celite bed. Charcoal bed was washed with hot acetic acid (100 ml). The filtrate was cooled to room temperature before being added to ice cold water (5 Lt). The quenched mass was stirred at 10° C. for 15 minutes. The yellow solid, which was formed, was collected at suction, washed with water till neutral and dried at 70° C. for 14 hrs. This gave the title compound, 36 gm, (85%) as a yellow solid.

MS-m/z M+H=307

NMR (200 MHz) DMSO; d 2.8 (t, 2H, CH2-Ar); d 3.46 (s, 2H, CH2—CO); d 3.79 (t, 2H CH2N)

d 6.6-7.02 (m, 3H, Ar—H); d 7.8 (s, 4H, Ar—H); d 10.3 (s, 1H, CONH).

Example—4A

Preparation of 4-(2'-phthalimido Ethyl)-1,3-dihydro-2H-indol-2-one (VI)

A 10 L pressure reactor was charged with dry Pd/C (30 gm), 4-(2'-phthalimidoethyl)-3-chloro-1,3-dihydro-2H-indol-2-one (300 gm, 0.882 mol), triethylamine (133 gm, 0.952 mol) and dimethylformamide (6 L). The reaction mixture was hydrogenated at 30-50° C. and 70-75 psi for 2 hours. The catalyst was filtered at 50° C. and filtrate was concentrated in vacuum. Water (1.5 L) was added to residue and slurry was stirred for 30 minutes at 30° C. The solids were filtered at suction and washed with water, and dried in oven at 60-70° C. to give title compound as yellow solid (225 gm, 83.3%).

Example—5

Preparation of 4-(2'-aminoethyl)-1,3-dihydro-2H-indol-2-one Hydrochloride (VI)

To a stirred suspension of 4-(2'-phthalimidoethyl)-1,3-dihydro-2H-indol-2-one (35 gm, 0.114 mol) in methanol (800 ml) was added a solution of hydrazine hydrate (18 ml, 0.369 mol) in methanol (75 ml). The reaction mixture was warmed to 40° C. and maintained at 40-42° C. for 17 hrs. Acetic acid (87 ml) was then charged before being heated to 60° C. The reaction mixture was stirred at 60° C. for further 30 minutes before being cooled to 0° C. The precipitate was filtered and the cake was washed with methanol (100 ml). The filtrate was concentrated to dryness and to the residue was added Isopropyl alcohol (250 ml) and ethyl acetate (150 ml). The solid suspension was stirred further for 2 hrs at 0-5° C. The brownish solid was filtered at suction, washed with ethyl acetate (100 ml) and dried at 60° C. for 5 hr. This gave the material 18 gm, (70%) of product as a brown solid. The solid was stirred with ethanolic HCl (100 ml) at 5-10° C. for 2 hrs and filtered at suction, solids washed with chilled (5° C.) ethanol. Faint brownish yellow solid mass isolated, which then dried in oven at 60° C. for 5 hrs. This gave title compound (12 gm) (75%).

MS-m/z M+H=177

NMR (200 MHz) DMSO; d 2.87-2.99 (m, 4H, N—CH$_2$ & Ar—CH$_2$); d 3.51 (s, 2H, CH$_2$-CO);

d 6.76 (d, 1H Ar—H); d 6.86 (d, 1H, Ar—H); d 7.15 (t, 1H, Ar—H); d 8.27 (s, 2H, NH$_2$); d 10.49 (s, 1H, CONH).

Example—6

Preparation of 4[2-(di-n-propylamino)ethyl]-1,3-dihydro-2-indol-2-one Hydrochloride I A mixture of 4(2'-aminoethyl)-1,3-dihydro-2H-indol-2-one hydrochloride (5 gm, 0.0235 mol), propionaldehyde (5 ml, 0.0687 mol) and 1 gm of 10% Pd/C (50% wet with water) in methanol (200 ml) was hydrogenated at 5 Kg/cm$^2$ hydrogen pressure at room temperature for 24 hrs. The mixture was filtered through celite bed and the bed was washed with methanol (20 ml). The filtrate was concentrated to dryness, slurried in ethanol (40 ml) at 5-10° C. The cream coloured solid was collected at suction, washed with ethanol (20 ml) and dried, Yield: 2.86 gm (41%) as a off white solid. Purity 90%

Example—6A

To a stirred clear solution of 4-[2-(di-n-propyl amino) ethyl]-1,3-dihydro-2-indol-2-one hydrochloride-I (2.86 gm, 0.084 mol), in water (25 ml) was added Sodium hydroxide solution (2.5 gm in 2.5 ml water) at 0 to 5° C. over a period of 30 min., raised the temperature to 25° C. to 35° C. extracted (2×25 ml) with MDC. To this MDC extract, Acetic anhydride (0.625 ml, 0.006 mol) was added dropwise at temperature 25° C. to 35° C. and maintain for 3 hrs at same temperature. The MDC layer was washed with 2×12.5 ml sodium bicarbonate solution followed by 12.5 ml water. MDC layer was evaporated on rotary evaporator under vacuum at 45° C. to 50° C. till complete removal of solvent. To the obtained residue, 12.5 ml of isopropyl alcohol was added and stirred for 10-15 min at 25° C. to 35° C. to a clear solution. The reaction mixture was further cooled to 5° C.-10° C. and to this chilled solution 9 ml of ethanolic hydrochloride was added dropwise to get precipitate of hydrochloride salt of the title compound and further dried. Yield: 2.12 gm (85%) as a bluish-offwhite solid, Purity 95%

MS-m/z=261

NMR (200 MHz) DMSO; d 0.92 (t, 6H, CH3); d 1.69 (m, 4H, —CH$_2$); d 3.01-3.15 (m, 8HN (CH$_2$)3, Ar—CH$_2$); d 3.55 (s, 2H, COCH$_2$); d 6.7 (d, 1H, Ar—H); d 6.8 (s, 1H, Ar—H); d 7.14 (t, 1H, Ar—H); d 10.78 (s, 1H, NH).

A pharmaceutical composition comprising a therapeutically effective amount of 4-[2-(di-n-propyl amino)ethyl]-1,3-dihydro-2H-indol-2-one or its salt is prepared by conventional methods.

A method of treating Parkinson's disease or cardiovascular disorders, the method comprising administering to a patient an effective amount of a product-by-process composition of matter comprising 4-(2-Dipropylaminoethyl)-1,3-dihydro-2H-indol-2-one or its salt wherein the said 4-(2-Dipropylaminoethyl)-1,3-dihydro-2H-indol-2-one or its salt manufactured by the said process.

Note that in the specification including claims, the phrase "a pharmaceutical composition" means at least one pharmaceutical composition (or may include more than one), suitable for treating Parkinson's disease or cardiovascular disorders respectively.

We claim:
1. A process for preparation of compound of structural formula (I)

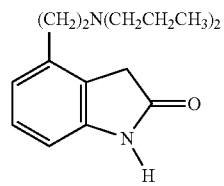

and its acid addition salts, particularly hydrochloride salt, which comprises the steps of:
a) Condensing a compound of formula II wherein X is a leaving group,

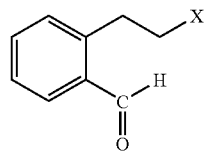

with alkali metal salt of an imide in a solvent to form compound of formula III

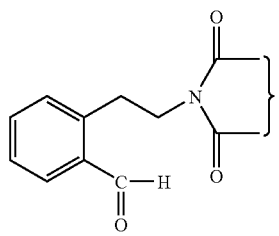

b) Treating compound of formula III with nitromethane in presence of RCOOH, R$^1$ NH$_2$ and HC(OR$^2$)$_3$ in a polar solvent to form a compound of formula IV, and wherein R is C$_{1-4}$ alkyl preferably methyl, R$^1$ is C$_{1-4}$ alkyl preferably butyl, R$^2$ is C$_{1-4}$ alkyl preferably methyl,

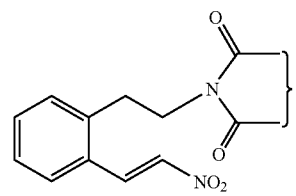

c) Treating compound of formula IV with FeCl3 and R$^3$ COCl, in solvent to form compound of formula V, wherein R$^3$ is C$_{1-4}$ alkyl preferably butyl,

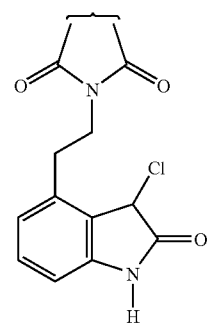

d) Treating compound of formula V with a hydrogen donor in presence of reduction catalyst in ethyl acetate, to form a compound of formula VI,

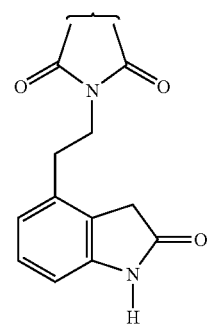

e) Treating compound of formula VI with hydrazine hydrate or alkali metal hydroxide followed by aqueous halo acid to form a compound of formula VII,

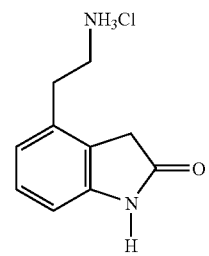

f) Treating compound VII with propionaldehyde under reducing conditions

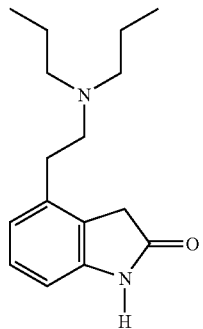

in presence of a reduction catalyst in solvent to form a compound of formula (I),
g) Conversion of compound of formula I to its hydrochloride salt,
h) Purification of hydrochloride salt of compound of formula I.

2. A process as per claim 1 where X is halo most preferred being bromo.

3. A process as claimed in claim 1 wherein the solvent used in step A is dipolar aprotic or a lower aliphatic alcohol or an aromatic hydrocarbon or aliphatic ketone or a mixture thereof.

4. A process as claimed in claim 1 wherein solvent used in step A is dimethyl sulphoxide.

5. A process as claimed in claim 1 wherein solvent used in step A is dimethyl formamide.

6. A process as claimed in claim 1 wherein solvent used in step A is acetone.

7. A process as claimed in claim 1 wherein solvent used in step A is mixture of dimethyl sulphoxide, dimethyl formamide and acetone.

8. A process as claimed in 1 wherein solvent used in step A is methanol, ethanol, propanol, isopropanol, r-butanol, iso-butanol, t-butanol.

9. A process as claimed in claim 1 wherein the solvent used in step A is toluene or benzene.

10. A process as claimed in claim 1 wherein the solvent used in step A is acetone or ethylmethyl ketone.

11. A process as claimed in claim 1 wherein the solvent used in step B is selected from lower aliphatic alcohols.

12. A process as claimed in claim 11 wherein said solvent is selected from methanol or ethanol or mixture thereof.

13. A process as claimed in claim 1, wherein said solvent used in step C is Chloroform or Carbon tetrachloride or Dichloroethane or a mixture thereof.

14. A process as claimed in 1 wherein hydrogen donor used in step D is either hydrogen or sodium hypophosphite or a formate.

15. A process as claimed in claim 1 wherein said catalyst used in step D is 5% to 20% palladium on charcoal.

16. A process as claimed in claim 15 wherein the percentage for palladium on charcoal is 10%.

17. A process as claimed in claim 1 wherein said solvent used in step F is methanol.

18. A process as claimed in claim 1 wherein said solvent used in step F is ethanol.

19. A process as per claim 1 wherein the catalyst used in step F is 5% to 20% palladium on charcoal.

20. A process as claimed in claim 19 wherein the percentage for palladium on charcoal is 10%.

21. A process as claimed in claim 1 wherein the reducing conditions used in step F comprise of hydrogen under pressure in the range of 0 to 10 kg/cm$^2$.

22. A process as claimed in claim 21 wherein the hydrogen pressure conditions is between 4 to 6 kg/cm$^2$.

23. A process as claimed in claim 1 wherein the alkali metal salt of an imide used in step A is potassium phthalimide.

24. A process as claimed in claim 1 wherein said catalyst used in step D is Raney Nickel.

* * * * *